US011959914B2

(12) United States Patent
Takakura et al.

(10) Patent No.: US 11,959,914 B2
(45) Date of Patent: Apr. 16, 2024

(54) AUTOMATIC ANALYZER AND ANALYSIS METHOD (71) Applicants: HITACHI HIGH-TECH CORPORATION, Tokyo (JP); ROCHE DIAGNOSTICS OPERATIONS, INC., Indianapolis, IN (US)

(72) Inventors: Tatsuki Takakura, Tokyo (JP); Kenta Imai, Tokyo (JP); Takaaki Hagiwara, Tokyo (JP); Yoshihiro Yamashita, Tokyo (JP); Taku Sakazume, Tokyo (JP); Beatus Ofenloch-Haehnle, Mannheim (DE); Michaela Windfuhr, Mannheim (DE); Ursula Pauselius-Fuchs, Mannheim (DE); Rita Haerteis, Mannheim (DE)

(73) Assignees: HITACHI HIGH-TECH CORPORATION, Tokyo (JP); ROCHE DIAGNOSTICS OPERATIONS, INC., Indianapolis, IN (US)

( * ) Notice: Subject to any disclaimer, the term of this patent is extended or adjusted under 35 U.S.C. 154(b) by 241 days.

(21) Appl. No.: 16/652,698

(22) PCT Filed: Jan. 29, 2019

(86) PCT No.: PCT/JP2019/002852
§ 371 (c)(1),
(2) Date: Apr. 1, 2020

(87) PCT Pub. No.: WO2019/176341
PCT Pub. Date: Sep. 19, 2019

(65) Prior Publication Data
US 2020/0240981 A1 Jul. 30, 2020

(30) Foreign Application Priority Data
Mar. 16, 2018 (JP) ................... 2018-048754

(51) Int. Cl.
G01N 33/543 (2006.01)
G01N 35/02 (2006.01)
(52) U.S. Cl.
CPC ........... G01N 33/543 (2013.01); G01N 35/02 (2013.01)
(58) Field of Classification Search
None
See application file for complete search history.

(56) References Cited

U.S. PATENT DOCUMENTS

| 5,610,069 | A | * | 3/1997 | Clark | ................. | B01L 3/08 |
| | | | | | | 422/562 |
| 2004/0209318 | A1 | * | 10/2004 | Adamczyk | ............. | C07K 16/44 |
| | | | | | | 435/7.92 |
| 2004/0209375 | A1 | * | 10/2004 | Diby | ................. | G01N 35/02 |
| | | | | | | 422/67 |
| 2005/0079520 | A1 | * | 4/2005 | Wu | ................. | C12Q 1/6834 |
| | | | | | | 435/6.1 |
| 2008/0023388 | A1 | * | 1/2008 | Cho | ................. | G01N 33/54326 |
| | | | | | | 210/222 |
| 2011/0192726 | A1 | * | 8/2011 | Chen | ................. | G01N 33/5438 |
| | | | | | | 204/547 |
| 2012/0171662 | A1 | | 7/2012 | Broyer et al. | | |
| 2013/0210654 | A1 | * | 8/2013 | Christopher-Hennings | ................. | |
| | | | | | | G01N 33/6863 |
| | | | | | | 436/501 |
| 2015/0330986 | A1 | * | 11/2015 | Grote | ................. | G01N 33/582 |
| | | | | | | 436/501 |
| 2016/0305949 | A1 | * | 10/2016 | Rabbani | ................. | C12Q 1/485 |
| 2016/0312266 | A1 | * | 10/2016 | Liu | ................. | C12Q 1/6806 |
| 2018/0071740 | A1 | | 3/2018 | Brueckner et al. | | |

FOREIGN PATENT DOCUMENTS

| CN | 103728429 A | 4/2014 |
| CN | 104395760 A | 3/2015 |
| JP | 2013-505010 A | 2/2013 |
| JP | 2015-55552 A | 3/2015 |
| WO | 2014/002952 A1 | 1/2014 |
| WO | 2016/193219 A1 | 12/2016 |

OTHER PUBLICATIONS

International Search Report of PCT/JP2019/002852 dated Apr. 23, 2019.
Chinese Office Action received in corresponding Chinese Application No. 201980004946.6 dated Mar. 1, 2023.

* cited by examiner

Primary Examiner — Ann Montgomery
(74) Attorney, Agent, or Firm — MATTINGLY & MALUR, PC (57) ABSTRACT

The automatic analyzer includes: a sample dispensing unit that dispenses a sample into a reaction vessel; a reagent dispensing unit that dispenses a reagent into the reaction vessel; a control unit that controls the sample dispensing unit and the reagent dispensing unit; and a measurement unit that measures a mixed solution of the sample and the reagent mixed in the reaction vessel. The reagent includes three types of reagents of: a first reagent that specifically binds to an antigen in the sample; a second reagent that specifically binds to a site different from that to which the first reagent binds with respect to the antigen and has a label to be detected by the measurement unit; and a third reagent that specifically binds to a site different from the binding site of the first reagent and the antigen and contains insoluble carriers.

2 Claims, 9 Drawing Sheets

AUTOMATIC ANALYZER AND ANALYSIS METHOD

TECHNICAL FIELD

The present invention relates to an automatic analyzer and an analysis method.

BACKGROUND ART

In the present technical field, there is known a technique in which a reagent that specifically reacts to a substance to be analyzed is mixed in a sample to be analyzed to proceed a chemical reaction, the mixed solution in reaction is measured, and thus a physical quantity corresponding to the concentration of the substance to be analyzed is measured. However, depending on the conditions for the sample to be analyzed or the reagent, analysis accuracy is sometimes considerably degraded. As such conditions, there are the case in which reactions are promoted in a pseudo manner due to the influence of a nonspecific bond and the case in which actions are suppressed due to a reaction inhibitor in a sample. To this, an analysis method having the step of cutting a specific antigen-antibody complex to a substance to be analyzed is disclosed (see Patent Literature 1).

CITATION LIST

Patent Literature

Patent Literature 1: Japanese Unexamined Patent Application Publication No. 2015-55552

SUMMARY OF INVENTION

Technical Problem

According to Patent Literature 1, the specific antigen-antibody complex to the substance to be analyzed is cut, its supernatant is measured, and thus the influence of the nonspecific bond is removed. However, since the specific bond is cut after the reaction step is completed, there is a problem that in which a reaction inhibitor is present in the reaction step the removal of its influence fails.

Therefore, an object of the present invention is to provide an automatic analyzer that can suppress influence due to reaction inhibitors and can improve analysis accuracy.

Solution to Problem

An automatic analyzer according to an aspect of the present invention includes a sample dispensing unit that dispenses a sample into a reaction vessel, a reagent dispensing unit that dispenses a reagent into the reaction vessel, a control unit that controls the sample dispensing unit and the reagent dispensing unit, and a measurement unit that measures a mixed solution of the sample and the reagent mixed in the reaction vessel. The reagent includes three types of reagents of: a first reagent that specifically binds to a substance to be analyzed in the sample, a second reagent that specifically binds to a site different from that to which the first reagent binds with respect to the substance to be analyzed and has a label to be detected by the measurement unit, and a third reagent that specifically binds to a site different from the binding site of the first reagent and the substance to be analyzed and contains insoluble carriers. The control unit controls to mix the first reagent and the third reagent with each other in the reaction vessel and to mix the sample and the second reagent with each other in the reaction vessel after a lapse of predetermined time.

Advantageous Effects of Invention

According to the present invention, an automatic analyzer that can suppress influence due to reaction inhibitors and can improve analysis accuracy can be provided.

DESCRIPTION OF EMBODIMENTS

In the following, embodiments will be described with reference to the drawings.

EXAMPLE 1

Figure 1:
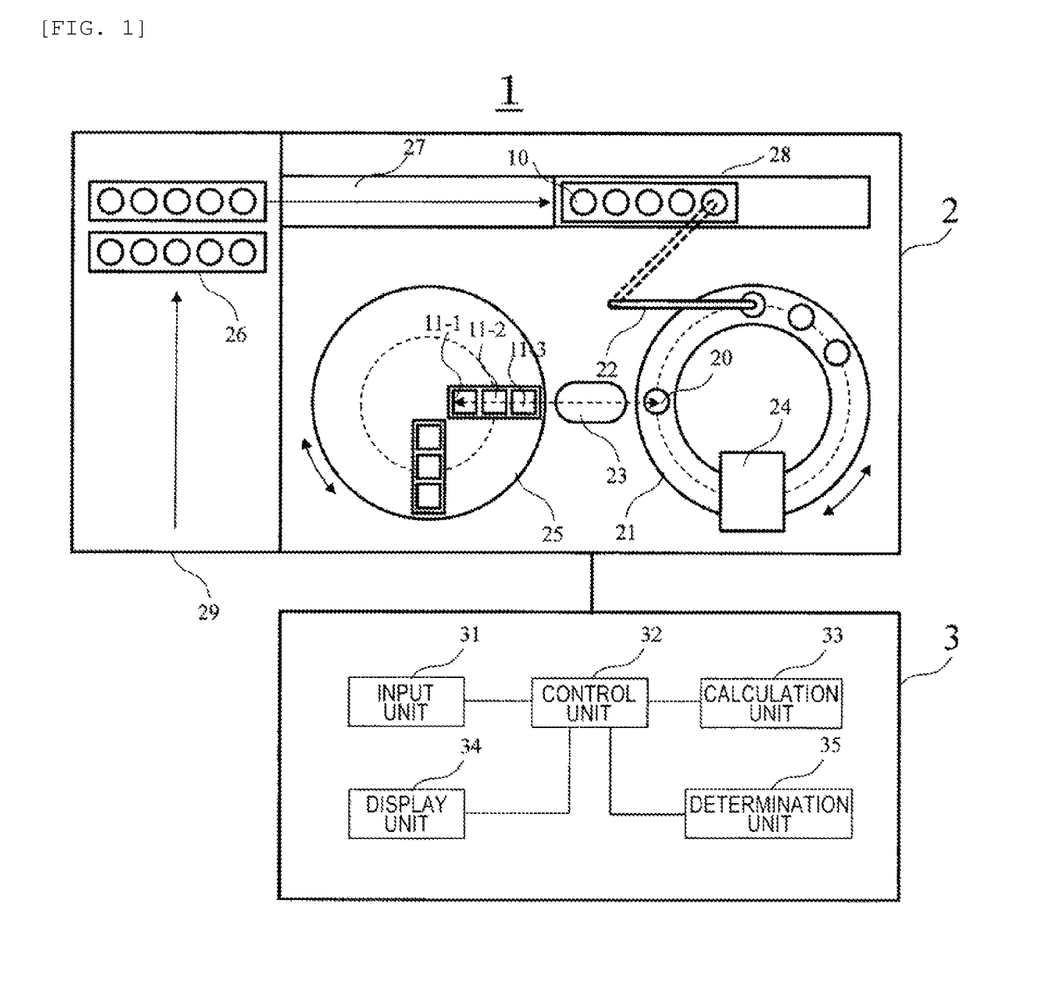
FIG. 1 is a diagram illustrating an automatic analyzer.

FIG. 1 is a diagram illustrating an automatic analyzer. This automatic analyzer 1 is formed of a measurement mechanism 2 and a control mechanism 3. These are electrically connected. The control mechanism 3 controls the measurement mechanism 2, and the measurement mechanism 2 feed-backs the obtained analysis result to the control mechanism 3.

The measurement mechanism 2 includes an introduction unit 29 that introduces a sample to be analyzed (in the following, referred to as a sample), a sample container 10, a reaction vessel 20 that accommodates reagent containers 11 (a first reagent container 11-1, a second reagent container 11-2, and a third reagent container 11-3) and a mixed solution of a sample and a reagent, an incubator 21 that holds the reaction vessel 20 to promote the reaction of the mixed solution, a sample dispensing unit 22 that dispenses a sample to the reaction vessel 20, a reagent dispensing unit 23 that dispenses a reagent to the reaction vessel 20, a measurement unit 24, a reagent holding unit 25 that holds the reagent container 11, a sample accommodating unit 26 that accommodates the sample container 10, a sample conveying unit 27 that conveys the sample accommodating unit 26, and a standby position 28 that causes a sample to wait to be dispensed to the reaction vessel 20.

The sample accommodating unit 26 holds one or more sample containers 10. The sample accommodating unit 26 maybe a rack system that simultaneously conveys a plurality of sample containers 10 as illustrated in the drawing, or may be a holder system that conveys sample containers one by one. The sample conveying unit 27 conveys the sample housing unit 26 introduced into the introduction unit 29 by an operator, for example, to the standby position 28 in the order of performing analyses.

The sample in the sample container 10 is sucked by the capacity specified by the sample dispensing unit 22, and is discharged to the reaction vessel 20. The reagent in the reagent container 11 is sucked by the capacity specified by the reagent dispensing unit 23, and is discharged to the reaction vessel 20. In this manner, the sample and the reagent are mixed with each other, after a lapse of a predetermined time, the mixed solution is physically measured at the measurement unit 24, and thus a substance to be analyzed (in the following, an antigen) in the sample is quantified.

The control mechanism 3 includes an input unit 31, a control unit 32, a calculation unit 33, a display unit 34, and a determination unit 35. The operator inputs analysis contents to the input unit 31. The control unit 32 controls the introduction unit 29, the incubator 21, the sample dispensing unit 22, the reagent dispensing unit 23, the measurement unit 24, the reagent holding unit 25, the sample housing unit 26, and the sample conveying unit 27 corresponding to the analysis contents inputted to the input unit 31. As described later, the control unit 32 includes a first mode that implements a first reaction step and a second mode that performs a second reaction step. The calculation unit 33 calculates an analytical value based on the physical quantity measured at the measurement unit 24. The display unit 34 displays the status of the progress of analysis, analytical values for completed analysis, and any other parameter, and notifies the operator. The determination unit 35 determines whether the analysis result is affected by the influence of a reaction inhibitor, described later, based on the calculated analytical value. Note that, in the case in which this determination is not performed, the determination unit 35 may be eliminated.

The incubator 21 and the reagent holding unit 25 are desirably a disk-shaped mechanism that can adjust the arrangement of containers by rotational motion, but this configuration is non-limiting. The sample dispensing unit 22 and the reagent dispensing unit 23 are described as mechanisms by rotational motion and linear motion. However, the sample dispensing unit 22 and the reagent dispensing unit 23 may be any mechanism that can perform appropriate suction and can move to appropriate discharge positions. In regard to the sample dispensing unit 22 and the reagent dispensing unit 23, one dispensing mechanism may have functions of these units.

Figure 2:
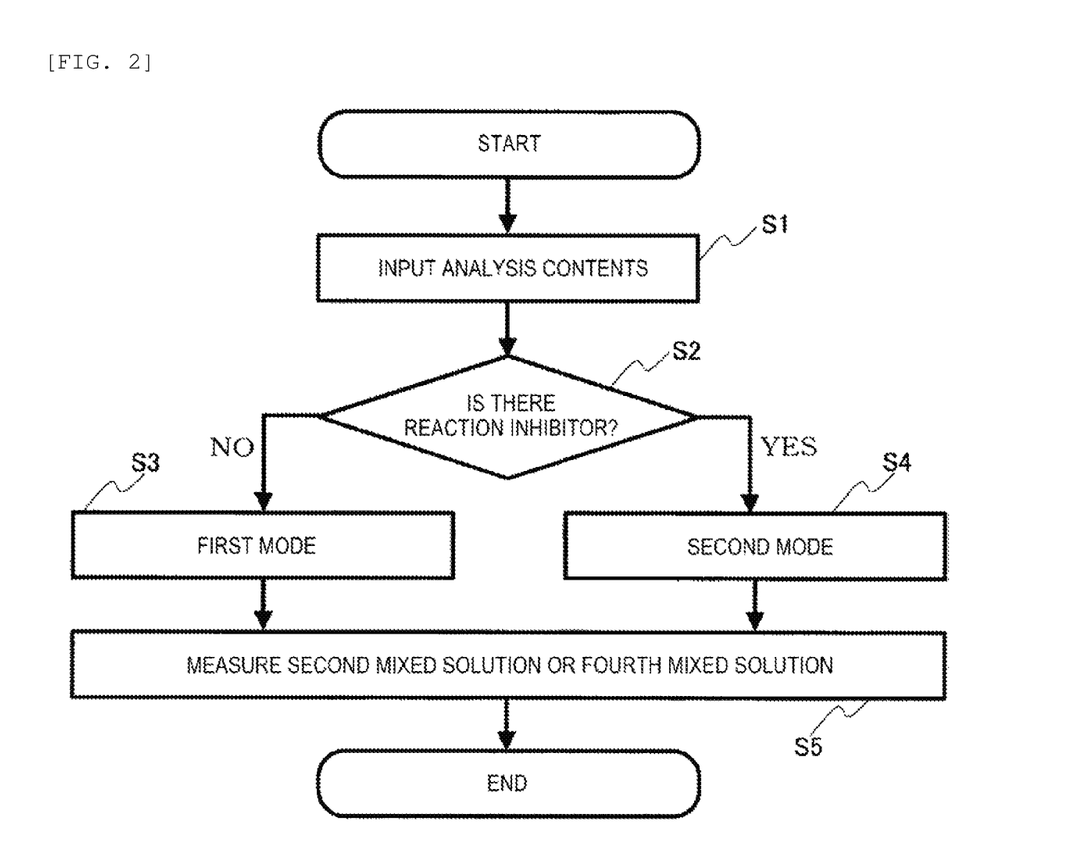
FIG. 2 is a flowchart of analysis.

FIG. 2 is a flowchart of analysis. First, the operator inputs analysis contents of a sample through the input unit 31 (S1). The operator determines the selection of Step S3 or S4, described later, for analyses beforehand corresponding to analysis items or the state of a sample, and contains the determined contents in the analysis contents to be inputted.

Subsequently, the control unit 32 determines whether a reaction inhibitor is present in sample based on the inputted analysis contents (S2). Note that, determination may be made based on predetermined conditions, not based on the input by the operator. In the case in which it is determined that no reaction inhibitor is present, the first mode is performed (S3), whereas in the case in which it is determined that a reaction inhibitor is present, the second mode is performed (S4). The measurement unit 24 measures a second mixed solution generated in S3 or a fourth mixed solution generated in S4 (S5).

Figure 3:
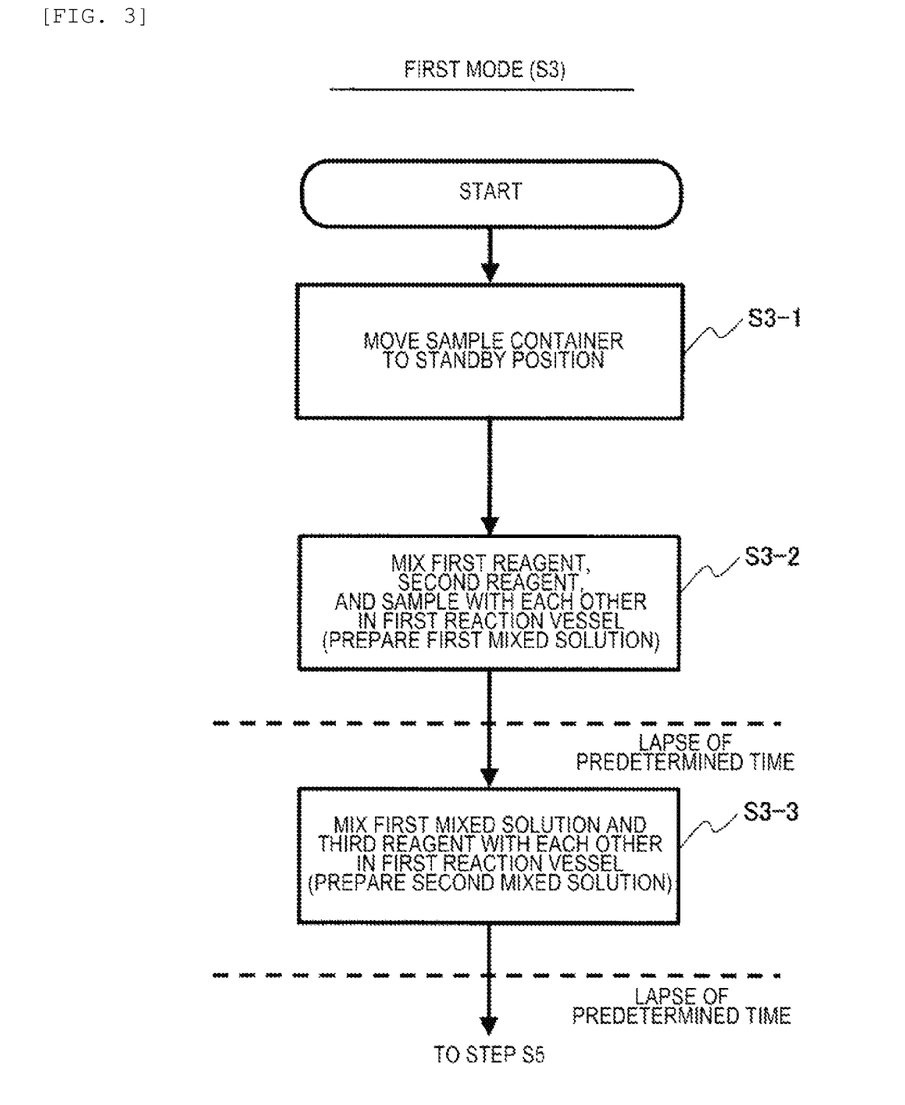
FIG. 3 is a flowchart of a first mode.

FIG. 3 is a flowchart of the first mode that implements the first reaction step. The first mode implements the first reaction step including the step of moving the sample container 10 at the standby position 28 (S3-1), the step of dispensing the first reagent and the second reagent to a first reaction vessel using the reagent dispensing unit 23 and dispensing the sample to the first reaction vessel using the sample dispensing unit 22 to prepare a first mixed solution made of the first reagent, the second reagent, and the sample (S3-2), and the step of dispensing a third reagent to the first reaction vessel using the reagent dispensing unit 23 to prepare a second mixed solution made of the first mixed solution and the third reagent (S3-3). After S3-2, S3-3 is performed after a lapse of a predetermined time, and after S3-3, S5 in FIG. 2 is performed after a lapse of a predetermined time.

Figure 4:
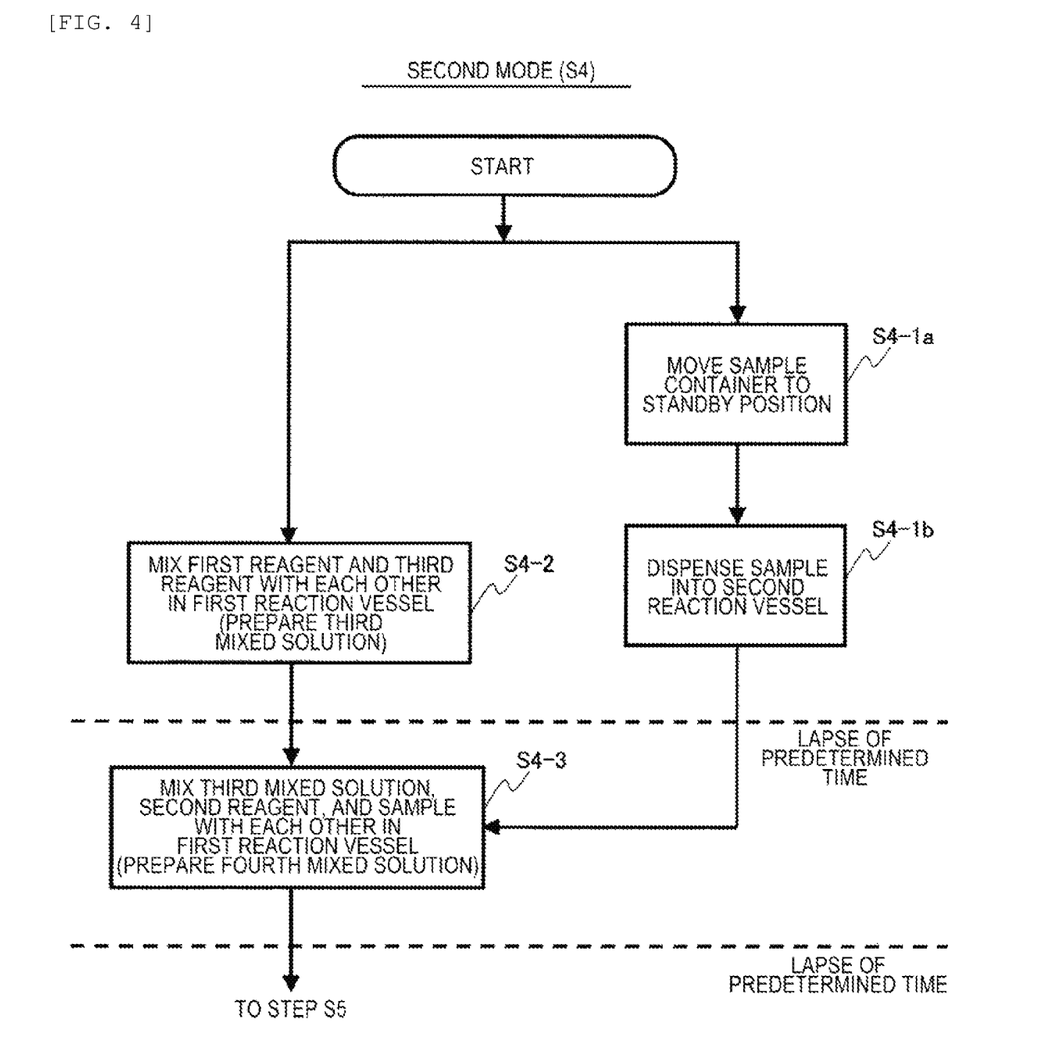
FIG. 4 is a flowchart of a second mode.

FIG. 4 is a flowchart of the second mode that implements the second reaction step. The second mode implements the second reaction step including the step of moving the sample container 10 at the standby position 28 (S4-1a), the step of dispensing the sample to a second reaction vessel using the sample dispensing unit 22 (S4-1b), the step of dispensing the first reagent and the third reagent to the first reaction vessel using the reagent dispensing unit 23 to prepare a third mixed solution made of the first reagent and the third reagent (S4-2), and the step of dispensing the second reagent to the first reaction vessel using the reagent dispensing unit 23 and dispensing the sample in the second reaction vessel to the first reaction vessel using the sample dispensing unit 22 to prepare a fourth mixed solution made of the third mixed solution, the second reagent, and the sample (S4-3). After S4-2, S4-3 is performed after a lapse of a predetermined time, and after S4-3, S4 in FIG. 2 is performed after a lapse of a predetermined time.

Here, the reagent used for analysis is unknown until a type of sample is confirmed. In the present embodiment, since the reagent used for analysis is confirmed by the arrival of the sample at the standby position 28, S4-1a has to be performed before S4-2. Therefore, in the second mode, the subsequent analysis is not enabled to start until dispensing the sample is completed in S4-3, resulting in a problem that analysis time is prolonged. However, in S4-1b, the sample is first dispensed to the second reaction vessel that is different from the first reaction vessel in which the sample and the reagent are mixed with each other, the standby position 28 is available for subsequent analysis, and thus prolonging analysis time can be suppressed at the minimum.

Figure 5:
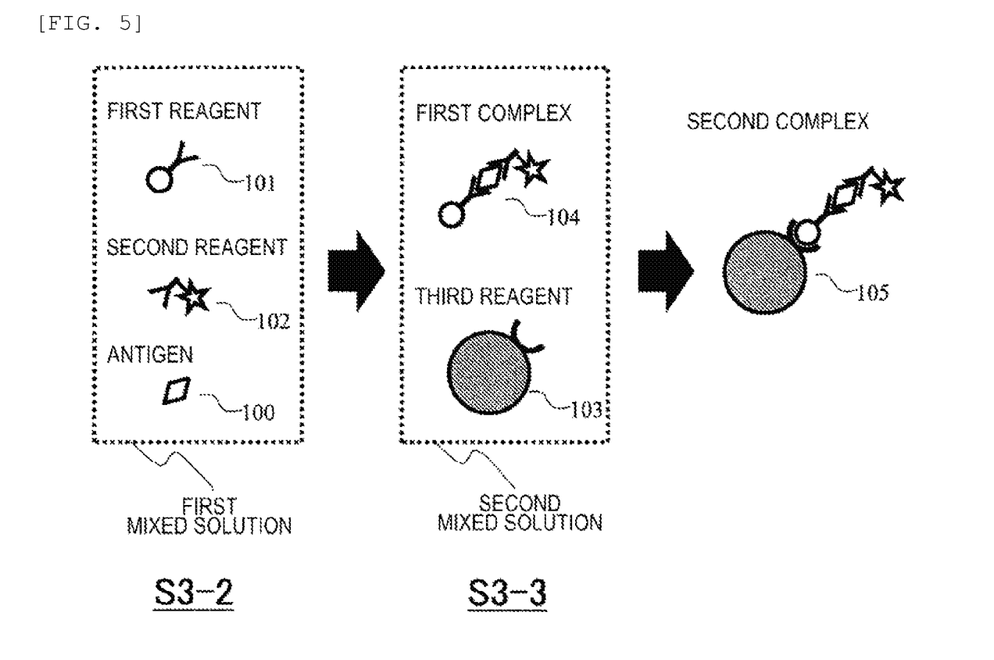
FIG. 5 is a reaction process in the first mode.

FIG. 5 is a diagram illustrating the reaction process in the first mode. A first reagent 101 (e.g. a biotinylated antibody) and a second reagent 102 (e.g. a labelled antibody) specifically bind to the different sites of an antigen 100. The first reagent 101 specifically binds to a third reagent 103 (e.g. a magnetic bead coated with streptavidin) made of an insoluble carrier that carries an antibody or an antigen on the particle surface. The second reagent 102 includes a substance that emits light detected by the measurement unit 24 (in the following, referred to as a label). The third reagent 103 is preferably a magnetic particle having a diameter of 300 nm or more, and is trapped by physical force, such as magnetic force, gravity, centrifugal force, and fluid resistance force.

In S3-2, the first reagent 101, the second reagent 102, and the antigen 100 are mixed with each other to prepare the first mixed solution. When a chemical reaction proceeds, the first reagent 101, the second reagent 102, and the antigen 100 specifically bind to form a first complex 104. In S3-3, the third reagent is added to the first mixed solution to prepare the second mixed solution. When a chemical reaction proceeds, the first complex 104 and the third reagent 103 specifically bind to form a second complex 105. After that, in the separation step of removing a supernatant (B/F separation), unreacted components in the mixed solution are removed, and only the label of the second reagent 102 that binds to the third reagent 103 is measured (S5).

Figure 6A:
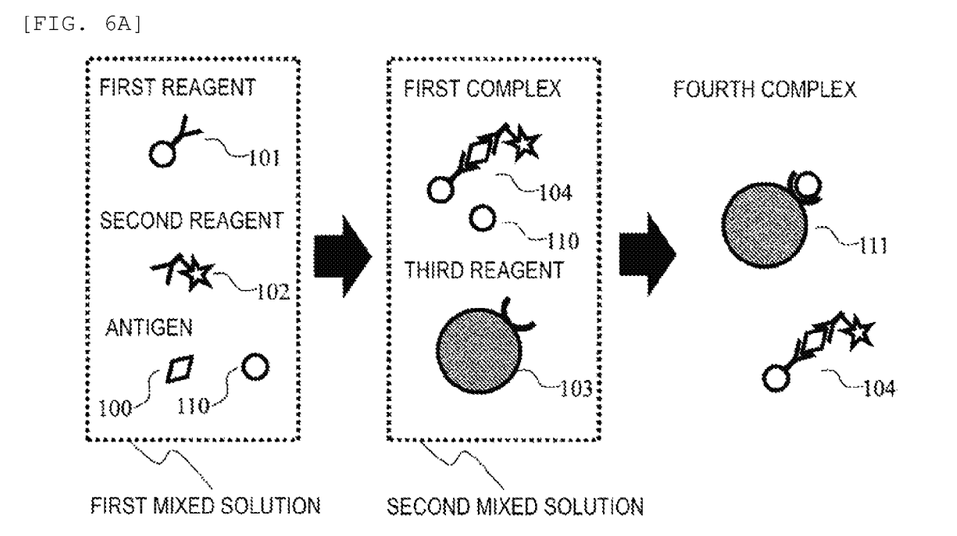
FIG. 6A is a diagram illustrating a reaction process when a reaction inhibitor is contained (Comparative Example).

FIG. 6 is a diagram illustrating a reaction process in the case in which a reaction inhibitor 110 having a chemical structure similar to the binding site of the first reagent 101 to the third reagent 103 is present. In FIG. 6A, the process is similar to that in FIG. 5 until the first complex 104 is formed. Here, the third reagent is added to the first mixed solution to prepare the second mixed solution (S3-3). When a chemical reaction proceeds, any of the first complex 104 or the reaction inhibitor 110 specifically binds to the binding site of the third reagent 103.

Here, in the case in which the third reagent 103 binds to the reaction inhibitor 110, a fourth complex 111 is formed. So, the first complex 104 is not trapped on the surface of the third reagent 103, and the first complex 104 is in the liberated state in the second mixed solution. When the separation step is performed in this state, the liberated first complex 104 is removed. Therefore, the amount of labels contributing to measurement is reduced, compared with the case in which no reaction inhibitor is contained in a sample, resulting in the degradation of measurement values.

Figure 6B:
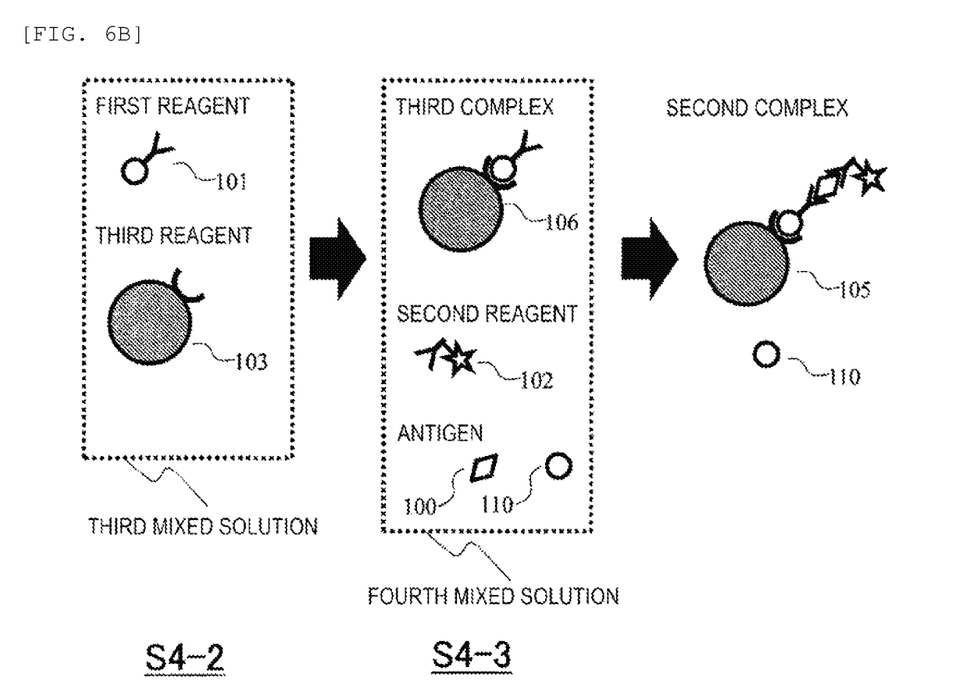
FIG. 6B is a diagram illustrating a reaction process when a reaction inhibitor is contained (second mode).

On the other hand, as illustrated in FIG. 6B (the second mode), the first reagent 101 and the third reagent 103 are mixed with each other to prepare the third mixed solution (S4-2). When a chemical reaction proceeds, the first reagent 101 and the third reagent 103 specifically bind to form a third complex 106. The sample including the second reagent and the antigen 100 is mixed with the third mixed solution to prepare the fourth mixed solution (S4-3). When a chemical reaction proceeds, the third complex 106, the second reagent 102, and the antigen 100 specifically bind to form the second complex 105. So, since the first reagent 101 already binds to the specific binding site of the third reagent 103, the reaction inhibitor 110 fails to bind. Therefore, in S4, the second complex 105 can be formed without affecting the influence of the reaction inhibitor 110. At the measurement unit 24, only the labels in the second complex 105 are measured (S5).

As described above, any of Step S3 or S4 is performed corresponding to the presence or absence of the reaction inhibitor, and thus the influence due to reaction inhibitors can be suppressed, and analysis accuracy can be improved.

Figure 7:
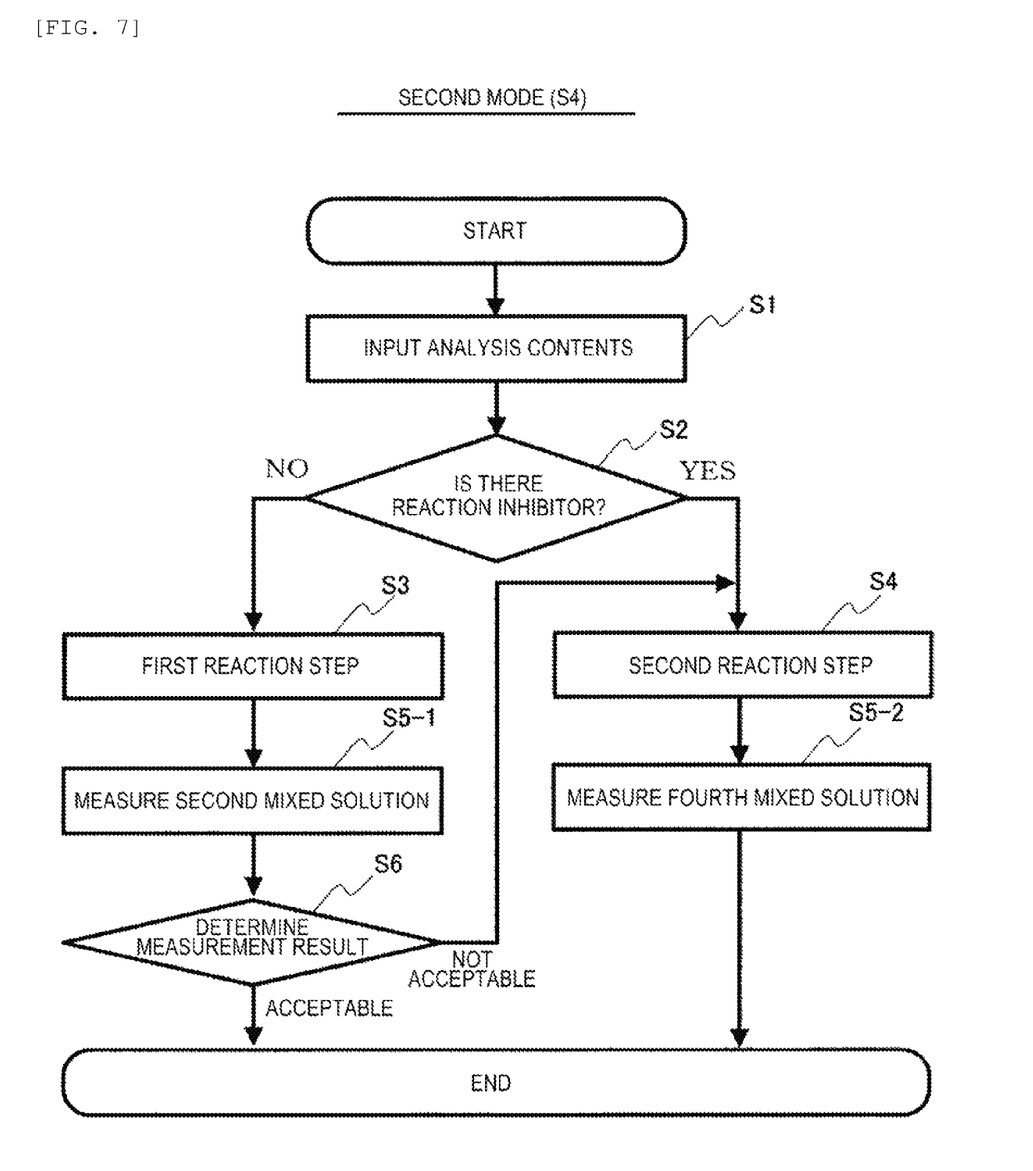
FIG. 7 is a flowchart in the case of using a determination unit.

FIG. 7 is a flowchart of the second mode in the case in which the determination unit 35 is used. In the following, only points different from FIG. 2 will be described. In the present flow, the second mixed solution is measured (S5-1), and whether to accept the result of the measurement is determined (S6). For example, the range of the analytical value assumed from the analysis contents is determined in advance, and the result is accepted when the analytical value is within a predetermined range or the result is unaccepted when the analytical value is out of a predetermined range.

In S6, in the case in which the determination is accepted, analysis is ended, whereas in the case in which the determination is unaccepted, S4 is performed on the same sample, the fourth mixed solution is measured (S5-2), and analysis is ended.

Here, in the case in which S3 is performed, as illustrated in FIG. 3, the number of the reaction vessels used in one analysis is one. On the other hand, in the case in which S4 is performed, as illustrated in FIG. 4, the number of the reaction vessels used in one analysis is two. Since the number of the reaction vessels simultaneously held by the incubator 21 has the upper limit, the analysis processing performance of the automatic analyzer 1 is degraded due to performing S4, compared with the case in which only S3 is performed. However, the flow in FIG. 7, S4 is performed only in the necessary case, and thus degradation in the analysis processing performance can be suppressed.

Note that, in the embodiment, the subsequent process is determined depending on the presence or absence of the reaction inhibitor. However, only the second mode in FIG. 2 may be performed on the premise that the reaction inhibitor is present.

EXAMPLE 2

Figure 8:
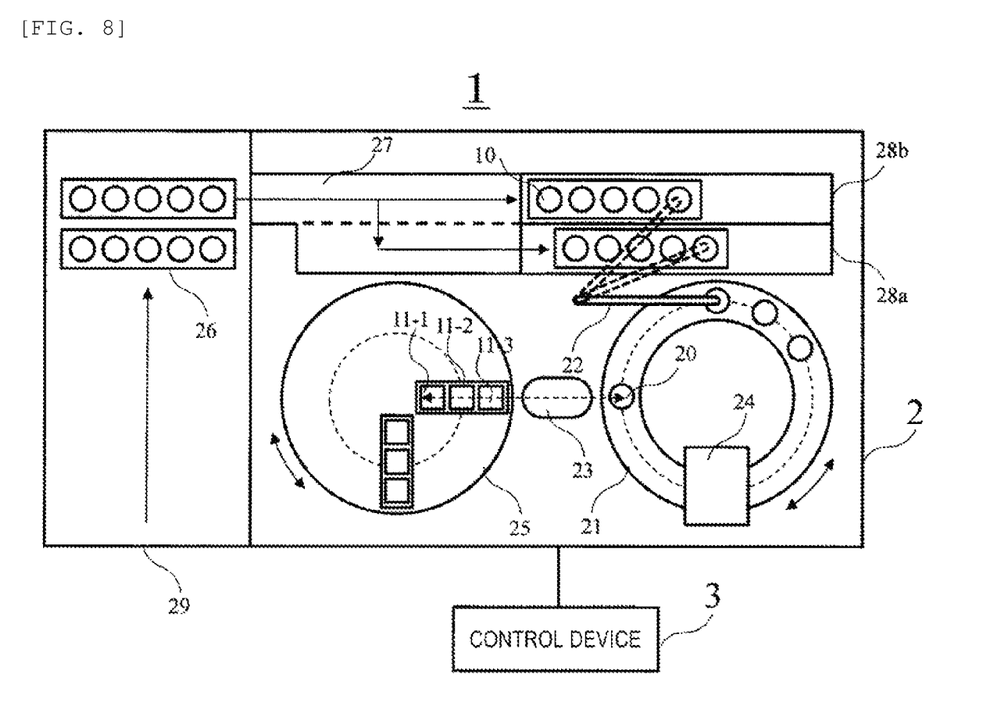
FIG. 8 is a diagram illustrating an automatic analyzer according to Example 2.

FIG. 8 is a diagram illustrating an automatic analyzer according to Example 2. The point different from Example 1 is that two standby positions, a first standby position 28a and a second standby position 28b, are provided. A sample that is dispensed in S3 is conveyed at the first standby position 28a, and a sample dispensed in S4 is conveyed at the second standby position 28b. desirably, the sample to which S3 is applied and the sample to which S4 is applied are held in different sample convey containers 26.

Figure 9:
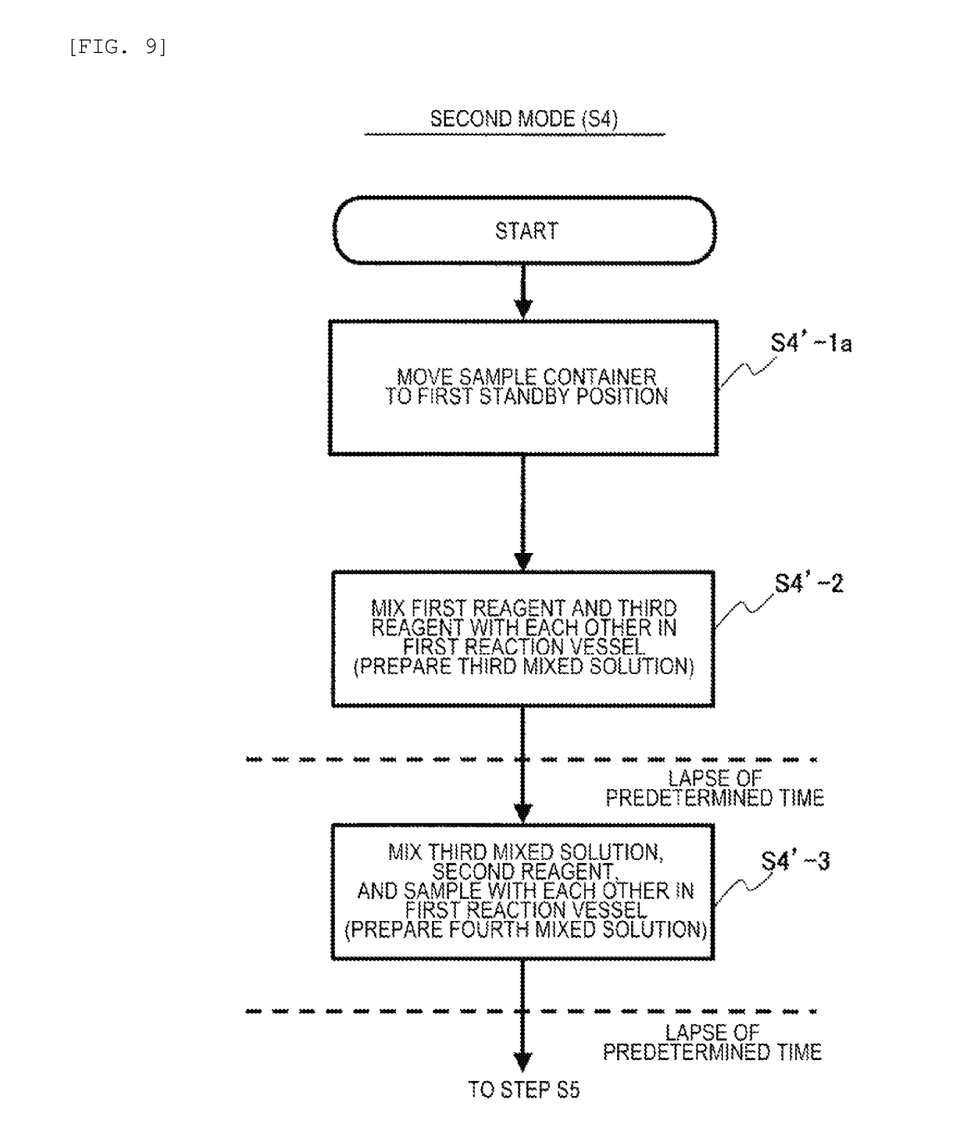
FIG. 9 is a flowchart of a second mode according to Example 2.

FIG. 9 is a flowchart of a second mode according to Example 2. S4' in Example 2 has the step of moving a sample container 10 to the first standby position 28a (S4'-1a), Step S4'-2 of dispensing a first reagent and a third reagent to a first reaction vessel using a reagent dispensing unit 23 to prepare a third mixed solution made of the first reagent and the third reagent, and Step S4'-3 of dispensing a second reagent to the first reaction vessel using the reagent dispensing unit 23 and dispensing the sample in the sample container 10 to the first reaction vessel using a sample dispensing unit 22 to prepare a fourth mixed solution made of the third mixed solution, the second reagent, and the sample. After S4'-2, S4'-3 is performed after a lapse of a predetermined time, and after S4'-3, S5 in FIG. 2 is performed after a lapse of a predetermined time.

In Example 1, the number of the reaction vessels used in one analysis is two. However, in Example 2, the number of the reaction vessels that are also used in the second mode is one, which is the same as the first mode. Accordingly, a plurality of analyses can be performed with no occurrence of degradation in the analysis processing performance.

REFERENCE SIGNS LIST

1: automatic analyzer
2: measurement mechanism
3: control mechanism
10: sample container
11: reagent container
20: reaction vessel
21: incubator
22: sample dispensing unit
23: reagent dispensing unit
24: measurement unit
25: reagent holding unit
26: sample accommodating unit
27: sample conveying unit
28: standby position
29: introduction unit
31: input unit
32: control unit
34: display unit
35: determination unit

The invention claimed is:

1. An automatic analyzer comprising:
a first standby position where a sample is waiting to be dispensed;
a sample dispensing unit configured to dispense the sample sucked from the first standby position into a reaction vessel;
a reagent dispensing unit configured to dispense first, second and third reagent into the reaction vessel;
an input unit configured to receive analysis contents inputted by an operator relating to a type of analysis to be performed on the sample;
a control unit configured to determine whether a reaction inhibitor having a chemical structure similar to a binding site of the first reagent, to the third reagent is expected to be present in the sample based on the inputted analysis contents and to control the sample dispensing unit and the reagent dispensing unit, wherein if the reaction inhibitor is not expected to be present, the sample is dispensed from the first standby position to a first reaction vessel according to a first mode and, if the reaction inhibitor is expected to be present, the sample is dispensed from the first standby position to a second reaction vessel or a second standby position according to a second mode;
a measurement unit configured to measure a mixed solution of the sample and the first second and third reagents, and
a determination unit configured to determine whether a result measured by the measurement unit is within a predetermined range determined in advance based on the analysis contents, wherein
the first reagent comprises a biotinylated antibody; the second reagent comprises a labelled antibody including a substance emitting light detectable by the measurement unit; and the third reagent comprises insoluble carriers carrying an antibody or antigen on a particle surface having a binding specificity for the first reagent,
if the control unit determines that the reaction inhibitor is not expected to be present, the control unit performs the first mode, in which the sample from the first standby position, the first reagent, and the second reagent are mixed with each other in the first reaction vessel to prepare a first mixed solution and the third reagent and the first mixed solution are mixed with each other in the first reaction vessel after a lapse of predetermined time to prepare a second mixed solution; and, if the control unit determines that the reaction inhibitor is expected to be present, the control unit performs the second mode in which the first reagent and the third reagent are mixed with each other in the first reaction vessel to prepare a third mixed solution and the sample from the second reaction vessel or the second standby position, the second reagent, and the third mixed solution are mixed with each other in the first reaction vessel after a lapse of predetermined time to prepare a fourth mixed solution, and
if the first mode is performed, and the determination unit has determined that the result measured by the measurement unit is not within the predetermined range determined in advance based on the analysis contents, the control unit is configured to control to perform the second mode.

2. An analysis method comprising:
a step of dispensing a sample into a first standby position;
a step of inputting analysis contents by an operator relating a type of analysis to be performed on to a sample;
a first determination step of determining whether a reaction inhibitor having a chemical structure similar to a binding site of the first reagent to the third reagent is expected to be present in the sample based on the inputted analysis contents, wherein if the reaction inhibitor is not expected to be present, the sample is dispensed from the first standby position to a first reaction vessel according to a first reaction process and, if the reaction inhibitor is expected to be present, the sample is dispensed from the first standby position to a second reaction vessel or a second standby position according to a second reaction process;
a step of, upon determining that the reaction inhibitor is expected to be present, performing the first reaction process which includes mixing the sample from the first standby position, a first reagent comprising a biotinylated antibody, and a second reagent comprising a labelled antibody including a substance emitting light detectable by the measurement unit in the first reaction vessel, for measuring a mixed solution of the sample and the first reagent to prepare a first mixed solution, and, after a lapse of predetermined time, mixing a third reagent, which comprises insoluble carriers carrying an antibody or antigen on a particle surface having a binding specificity for the first reagent, and the first mixed solution to prepare a second mixed solution in the first reaction vessel;
a step of, upon determining that the reaction inhibitor is not expected to be present, performing the second reaction process which includes mixing the first reagent and the third reagent to prepare a third mixed solution in a first reaction vessel, and, after a lapse of predetermined time, mixing the sample from the second reaction vessel or a second standby position, the second reagent, and the third mixed solution to prepare a fourth mixed solution;
a measurement step of measuring the second mixed solution or the fourth mixed solution; and
a second determination step of determining whether a result measured in the measurement step is within a predetermined range determined in advance based on the analysis contents, wherein
if the first reaction process is performed and the determination result is not within the predetermined range determined in advance based on the analysis contents in the second determination step, performing the second reaction process.

* * * * *